United States Patent
Majeed et al.

(10) Patent No.: US 10,421,734 B1
(45) Date of Patent: Sep. 24, 2019

(54) PROCESS FOR THE PREPARATION OF ENANTIOPURE 3-AMINO TETRAHYDROFURAN AND ITS SALTS

(71) Applicants: Muhammed Majeed, Edison, NJ (US); Kalyanam Nagabhushanam, East Windsor, NJ (US); Savita Ganjihal, Bangalore (IN); Rajendran Ramanujam, Bangalore (IN)

(72) Inventors: Muhammed Majeed, Edison, NJ (US); Kalyanam Nagabhushanam, East Windsor, NJ (US); Savita Ganjihal, Bangalore (IN); Rajendran Ramanujam, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 0 days.

(21) Appl. No.: 16/185,018

(22) Filed: Nov. 9, 2018

(30) Foreign Application Priority Data

Aug. 31, 2018 (IN) .............................. 201841032771

(51) Int. Cl.
*C07D 307/22* (2006.01)
*C07C 271/16* (2006.01)
*C07C 233/69* (2006.01)
*C07C 233/83* (2006.01)

(52) U.S. Cl.
CPC .......... *C07D 307/22* (2013.01); *C07C 233/69* (2013.01); *C07C 233/83* (2013.01); *C07C 271/16* (2013.01)

(58) Field of Classification Search
CPC ... C07D 307/22; C07C 233/83; C07C 233/69; C07C 271/16
USPC ........................................................ 549/480
See application file for complete search history.

(56) References Cited

U.S. PATENT DOCUMENTS 7,514,573 B2 * 4/2009 Majeed ................ C07D 307/22
549/480

OTHER PUBLICATIONS

Ramanujam et al , Expeditious novel routes to enantiopure 3-amino tetrahydrofuran hydrochloride, Terahedron: Asymmetry, 24, 2013, p. 663-668. (Year: 2013).*

* cited by examiner

*Primary Examiner* — Taylor V Oh

(57) ABSTRACT

Disclosed is simple, novel, scalable and environment friendly process for the preparation of enantiopure 3-amino tetrahydrofuran and its salts.

18 Claims, No Drawings

PROCESS FOR THE PREPARATION OF ENANTIOPURE 3-AMINO TETRAHYDROFURAN AND ITS SALTS

CROSS REFERENCE TO RELATED APPLICATION

This is a conventional U.S. patent application claiming priority from Indian Complete application no. 201841032771 filed on 31 Aug. 2018, the details of which are being incorporated herein by reference.

BACKGROUND OF THE INVENTION

Field of Invention

The present invention in general relates to 3-amino tetrahydrofuran. More specifically, the present invention relates to a novel process for the preparation of enantiopure 3-amino tetrahydrofuran and its salts.

Description of Prior Art

Enantiomerically pure molecules are gaining importance primarily in pharmaceutical and flavor-fragrance industry and this has led to a renaissance in synthetic methodology leading to very efficient methods of asymmetric synthesis (Walsh. P.; Kozlowski. M. Fundamentals of Asymmetric Catalysis; University Science Books: Sausalito, CA, 2009) and resolution methodology (Sakai, K., Hirayama, N., Tamura, R., Eds. Topics in Current Chemistry; Springer: Berlin, Heidelberg, 2006; Vol. 269). Another equally important technology of converting the naturally occurring chiral materials, the so-called chiral pool, offers a powerful, simple and often an economic solution for chiral materials, provided an efficient sequence of converting the chiral pool starting material to the desired end product can be designed.

While L-amino acids are naturally occurring and available economically, the advancement of biocatalytic technologies based on amino acylase, hydantoinase/carbamoylase, amidases has rendered access to D-amino acids (Groger, H. Enzyme Catalyzed Asymmetric Synthesis. In Catalytic Asymmetric Synthesis; Ojima, I., Ed.; John Wiley & Sons: Hoboken, N.J., 2010; p 269). Hence by simple selection of the suitable precursor amino acid, L- or D-amino acid, either of the desired optical antipodes of a final product can be obtained. One important advantage of using chiral pool starting materials is retrieving excellent optical purity to the final product if any adventitious reaction conditions that may lead to racemization in the reaction sequence are carefully avoided.

3-Amino tetrahydrofurans form an important substructure of several pharmacologically active compounds. They seem to extend certain desirable properties on the investigational drug structures. A series of G-protein coupled adenosine receptors mediate cardiac and antilipolytic activities. In particular, selective adenosine A1 receptors have received attention for possible antiarrhythmic activity. For example, 3-(R)-amino tetrahydrofuranyl moiety formed an integrative structural feature of selective, high affinity adenosine A1 receptor agonists (Elzein, E.; Kalla, R.; Li, X.; Perry, T.; Marquart, T.; Micklatcher, M.; Li, Y.; Wu, Y.; Zeng, D.; Zablocki, J. J. Med. Chem. Lett. 2007, 17, 161).

3-Amino tetrahydrofuranyl moiety also formed part of the structural features of orally bioavailable experimental CGRP receptor antagonists (Bell, I. M.; Bednar, R. A.; Fay, J. F.; Gallicchio, S. N.; Hochman, J. H.; McMasters, D. R.; Miller-Stein, C.; Moore, E. L.; Mosser, S. K.; Pudvah, N. T.; Quigley, A. G.; Salvatore, C. A.; Stump, C. A.; Theberge, C. R.; Wong, B. K.; Zartman, C. B.; Zhang, X. F.; Kane, S. A.; Graham, S. L.; Vacca, J. P.; Williams, T. M. Bioorg. Med. Chem. Lett. 2006, 16, 6164).

In spite of such extensive uses ((a) Miller, M. M.; Liu, Y.; Jiang, J.; Johnson, J. A.; Kamau, M.; Wang, Y.; Harikrishnan, L.; Wexler, R. R.; Poss, M. A.; Michael, L. R.; Salvati, M. E.; Nirschi, D. S.; Zhang, J.; Taylor, D. S.; Chen, A. Y. A.; Yin, X.; Adam, L. P.; Seethala, R.; Peterson, T. L.; Zvyaga, T.; Huang, C. S. Bioorg. Med. Chem. Lett. 2012, 22, 6503;

b) Goldstein, D. M.; Soth, M.; Gabriel, T.; Dewdney, N.; Kuglstatter, A.; Arzeno, H.; Chen, J.; Bingenheimer, W.; Dalrymple, S. A.; Dunn, J.; Farrell, R.; Frauchiger, S.; La Fargue, J.; Ghate, NI.; Graves, B.; Hill, R. J.; Li, F.; Litman, R.; Loe, B.; Mc-Intosh, J.; McWeeney, D.; Papp, E.; Park, J.; Reese, H. F.; Roberts, R. T.; Rotstein, D.; San Pablo, B.; Sarma, K.; Stahl, M.; Sung, M. L.; Suttman, R. T.; Sjogren, E. B.; Tan, Y.; Trejo, A.; Welch, M.; Weller, P.; Wong, B. R.; Zecic, H. J. Med. Chem., 2011, 54, 2255.

c) WO 2012/126084 d) WO 2012/117062) of 3-amino tetrahydrofuran in medicinal chemistry, commercially economical methods to obtain chiral forms are lacking and hard to practice.

L-Malic acid has been the starting material in obtaining optically pure isomers of 3-amino tetrahydrofuran through a lengthy sequence of reactions (Jin, L.; Shi, X. Chinese Patent CN 1,660,829, 2004; CAN 144,488,507). The large number of synthetic steps is a deterrent feature in this methodology.

In another method, L-methionine has been used as starting material (Barlos, K.; Papaioannou, D.; Patrianakou, S.; Sanida, C.; Tsegenidis, T. Chem. Commun. 1987, 474). In this approach L-methionine is converted to its N-tritylderivative in the first step. Use of trityl groups is generally avoided in large scale synthesis as they are expensive and generally need recovery of the tritylcarbinol for process economy.

A chemo enzymatic method of making 3-(S)-amino Tetrahydrofuran from racemic tetrahydrofuran-3-carboxylic acid has been described (Zhu, L.; Fan, H. Chinese Patent CN 1,814,769, 2006; CAN 145,504,171). This strategy involves handling of azides (for the conversion of —COOH functionality to —NH2) that is undesirable from safety point of view.

Asymmetric hydrogenation of hydrazone derivative of tetrahydrofuran-3-one has been reported recently that finally leads to chiral forms of 3-aminotetrahydrofuran. But under optimal conditions the maximum enantiomeric excess values of only 72% has been reported (Haddad, N.; Bo, Q.; Rodriguez, S.; Van der Veen, L.; Reeves, D. C.; Gonnella, N. C.; Lee, H.; Grinherg, N.; Ma, S.; Krishnamurthy, D.; Wunberg, T.; Senanayake, C. H. Tetrahedron Lett. 2011, 52, 3718).

A previous approach (U.S. Pat. No. 7,514,573) M. Majeed et al., Tetrahedron Asymmetry. 2013, 24, 663) uses the inherent chirality present in the easily accessible and economical starting materials, L-aspartic acid and L-Methionine. L-aspartic acid and L-Methionine were converted to a common intermediate, (S)-2-benzoylaminobutane 1,4-diol which was further cyclized and debenzoylated to isolate the product (S)-3-aminotetrahydrofuran as hydrochloride salt.

There are many commercial processes available for the preparation of 3-amino tetrahydrofuran in the literature with some disadvantages such as either they are multi steps or they are not commercially viable. Hence there is need to develop a commercially viable, safe, simple, single pot and scalable process for the large scale production of 3-amino tetrahydrofuran and its salts. The present invention fulfills this objective and provided further related advantages.

SUMMARY OF THE INVENTION

The present invention discloses novel synthetic schemes for the preparation of enantiopure 3-amino tetrahydrofuran. More specifically, the invention discloses simple, novel, scalable and environment friendly process for the preparation of enantiopure 3-amino tetrahydrofuran and its salts.

The present invention provides the following advantages.
1. The invention uses enantiopure starting material which is readily available
2. The present invention is economically viable and practical
3. The protecting group Benzyloxycarbonyl on deprotection in neutral condition gives product 3-amino tetrahydrofuran as free base which can be directly condensed as per the requirement
4. Further one can make (R)-3-amino tetrahydrofuran and racemic 3-amino tetrahydrofuran and its salts following the same sequence starting from D-Methionine and DL-Methionine.

Other features and advantages of the present invention will become apparent from the following more detailed description, taken in conjunction with the accompanying images, which illustrate, by way of example, the principle of the invention.

DETAILED DESCRIPTION OF THE MOST PREFERRED EMBODIMENT

In the most preferred embodiment, the present invention relates to a process for the preparation of (S)-3-Aminotetrahydrofuran hydrochloride represented by formula (I).

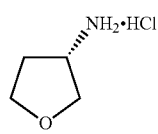

comprising the steps of
a) reacting (S)-2-aroylamino gamma-butyrolactone represented by the formula (II) with an acid halide/alcohol to get alkyl-(S)-2-aroylamino 4-halo butanoate represented by the formula (III).

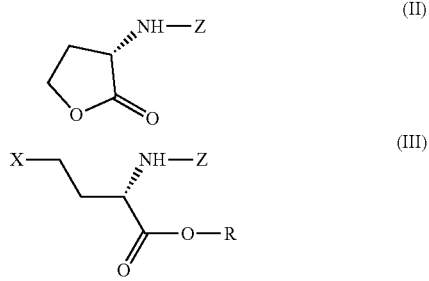

wherein,
'Z' is selected from benzoyl, o-, p- methylbenzoyl, o-, m-, p- chlorobenzoyl, o-, m-, p-methoxybenzoyl or p-toluenesulphonyl 'R' is selected from methyl, ethyl, n-propyl, isopropyl, butyl or isobutyl
b) reducing alkyl-(S)-2-aroylamino 4-halo butanoate of formula (III) using metal borohydride in a solvent to provide (S)-2-aroylainino 4-halo-1-butanol represented by the formula (IV).

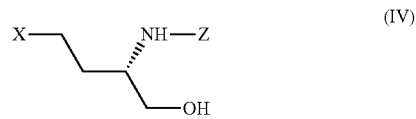

wherein,
'Z' is selected from benzoyl, o-, m-, p- methylbenzoyl, o-, m-, p- chlorobenzoyko-, m-, p-methoxybenzoyl or p-toluenesulphonyl.
'X' in is selected from Cl or Br
c) cyclizing (S)-2-Aroylamino 4-halo-1-butanol of formula (IV) using a base to obtain (3)-aroylamino tetrahydrofuran renresented by the formula (V)

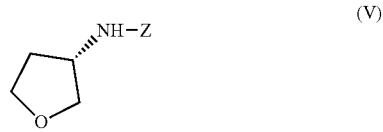

wherein,
'Z' is selected from benzoyl, o-, m-, p- methylbenzoyl, o-, m-, p- chlorobenzoyl,o-, m-, p-methoxybenzoyl or p-toluenesulphonyl.
d) removing the aroyl group of (3)-Aroylamino tetrahydrofuran with the formula (V) using metal hydroxide/alcohol medium followed by treatment with aqueous hydrochloric acid to get (S)-3-aminotetrahydrofuran hydrochloride represented by the formula (I).

In another preferred embodiment the invention relates to acid halide in step (a) is selected from acetyl chloride, acetyl bromide, thionyl chloride, thionyl bromide, propionyl chloride, propionyl bromide, butyryl chloride, butyryl bromide, isobutyryl chloride and isobutyryl bromide.

In yet another preferred embodiment the invention relates to alcohol in step (a) is selected from methanol, ethanol, n-propanol, isopropanol, butanol, isobutanol and sec.butanol.

In another preferred embodiment the invention relates to metal borohydride in step (b) is selected from lithium borohydride, sodium borohydride, potassium borohydride and zinc borohydride.

In yet another preferred embodiment the invention relates to solvent in step (b) is selected from methanol, ethanol, n-propanol and isopropanol.

In another preferred embodiment the invention relates to base in step (c) is selected from sodium hydroxide, potassium hydroxide, sodium carbonate, potassium carbonate, calcium hydroxide, barium hydroxide, magnesium hydroxide, triethylamine, diisopropyl ethylamine, pyridine and 4-dimethylamino pyridine.

In yet another preferred embodiment the invention relates to metal hydroxide in step (d) is selected from sodium hydroxide, potassium hydroxide, calcium hydroxide, barium hydroxide and magnesium hydroxide.

In another most preferred embodiment, the present invention relates to a process for the preparation of compound of formula (V)

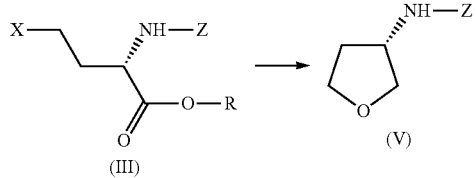

(V)

by reducing alkyl-(S)-2-aroylamino 4-halo butanoate of formula (III) and cyclizing to obtain (3)-aroylamino tetrahydrofuran represented by the formula (V)

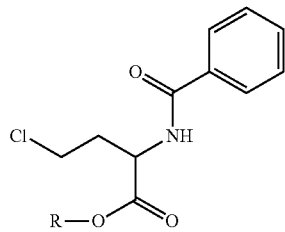

(III) → (V)

In yet another related embodiment the invention relates to a compound represented by the formula (VI).

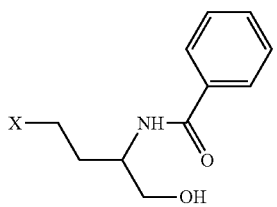

(VI)

wherein,
R in formula (VI) is selected from —CH3 or —C2H5

In another most preferred embodiment the invention relates to the compound of the formula (VIII), 2-benzoylamino 4-halo 1-butanol (VIII)

Wherein,
'X' in formula (VIII) is Cl or Br

In another most preferred embodiment the invention relates to a process for the preparation of (S)-3-Aminotetrahydrofuran hydrochloride represented by formula (I).

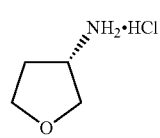

(I)

comprising steps of a) reacting (S)-2-benzyloxycarbonylamino gamma-butyrolactone represented by the formula (X) with an acid halide/alcohol to get alkyl (S)-2-benzyloxycarbonylamino-4-halo butanoate represented by the formula (XI).

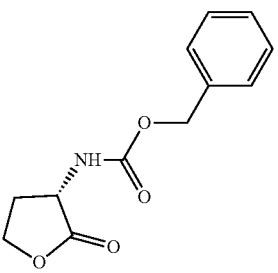

(X)

(XI)

wherein,
'R' is selected from methyl, ethyl, n-propyl, isopropyl, butyl or isobutyl
'X' is selected from Cl or Br b) reducing alkyl (S)-2-benzyloxycarbonylamino 4-halo butanoate of formula (XI) using metal borohydride in a solvent to provide (S)-2-benzyloxycarbonyl- 4-halo 1-butanol represented by the formula (XII).

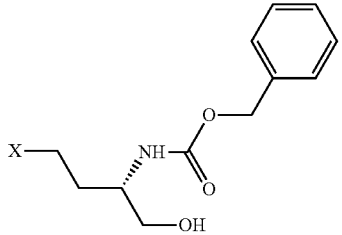

(XII)

wherein,
'X' is selected from Cl or Br c) cyclizing (S)-2-benzyloxycarbonyl 4-halo- 1-butanol of formula (XII) using a base to obtain (S)-benzyoxycarbonylamino tetrahydrofuran represented by the formula (XIII).

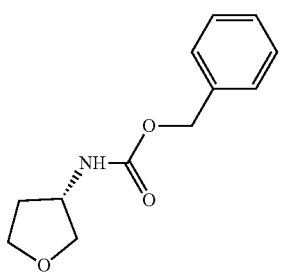

(XIII)

d) removing the benzyloxycarbonyl group of (S)-benzyoxycarbonylamino tetrahydrofuran represented by the formula (XIII) using Palladium/carbon or Raney nickel under hydrogen atmosphere in alcohol medium followed by separation of the catalyst and subsequent treatment with aqueous hydrochloric acid to get (S)-3-Aminotetrahydrofuran hydrochloride represented by the formula (I).

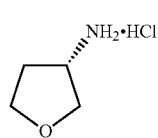

(I)

In another preferred embodiment the invention relates to acid halide in step (a) is selected from acetyl chloride, acetyl bromide, thionyl chloride, thionyl bromide, propionyl chloride, propionyl bromide, butyryl chloride, butyryl bromide, isobutyryl chloride and isobutyryl bromide.

In another preferred embodiment the invention relates to wherein alcohol in step (a) is selected from methanol, ethanol, n-propanol, isopropanol, butanol, isobutanol and sec.butanol.

In yet another preferred embodiment invention relates to metal borohydride in step (b) is selected from lithium borohydride, sodium borohydride, potassium borohydride and zinc borohydride.

In another preferred embodiment the invention relates to solvent in step (b) is selected from methanol, ethanol, n-propanol and isopropanol.

In yet another preferred embodiment invention relates to base in step (c) is selected from sodium hydroxide, potassium hydroxide, sodium carbonate, potassium carbonate, calcium hydroxide, barium hydroxide, magnesium hydroxide, triethylamine, diisopropyl ethylamine, pyridine and 4-dimethylamino pyridine.

In yet another most preferred embodiment the invention relates to the compositions of the formula (IX), 2-benzyloxycarbonylamino-4-halo 1-butanol

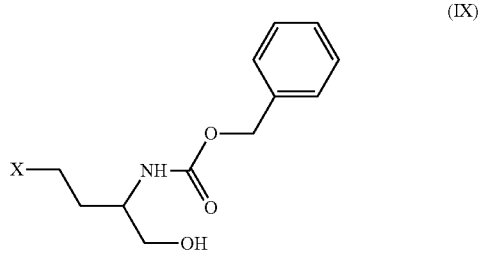

(IX)

wherein,
'X' in formula (IX) is Cl or Br

In yet another most preferred embodiment the invention relates to a process for the preparation of the compound with formula (XIII)

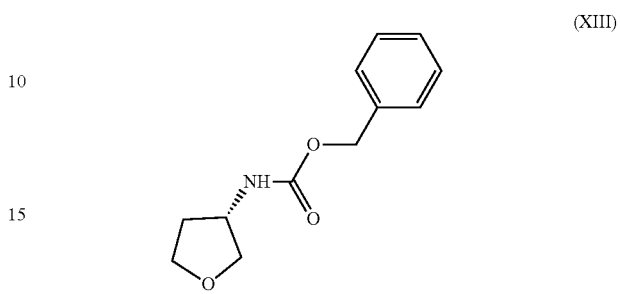

(XIII)

by reducing compound with formula (XI) and cyclizing to obtain compound with formula (XIII)

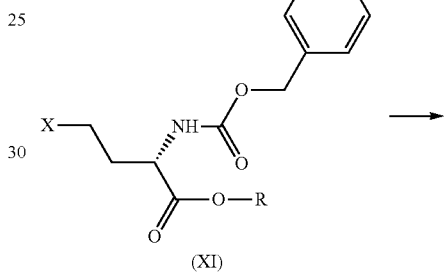

(XI)

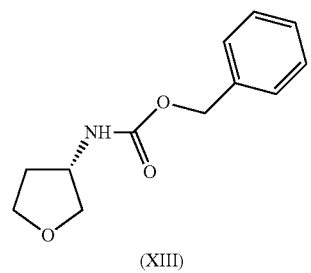

(XIII)

EXAMPLES

Example 1: Synthesis of (S)-2-Benzoylamino 4-chloro Butyric Acid Methyl Ester (3)

Dry methanol (200 ml) is taken and cooled to 0-5° C. Acetyl chloride (39.25g, 0.5 mol) is added drop wise at that temperature and stirred for 15 minutes. (S)-2-Benzoylamino γ-Butyrolactone (2) (20.5g, 0.1 mol) is added portion wise at >10° C. over a period of 30 minutes. The clear solution is stirred at RT for 15 hours for the complete reaction. The completion is confirmed by Thin layer chromatographic (TLC) analysis.

Once the reaction is complete, methanol is removed by distillation under vacuum and ice water is added. The product is extracted using methylene dichloride (MDC) and the organic layer is washed with water twice followed by brine solution. The organic layer is dried over sodium sulfate and concentrated completely. The product is precipitated by stirring with Hexane and filtered. Dried under vacuum to get the white solid product.

Yield: 24.5g
The product has the following characteristics.
Melting point: 76-79° C.
SOR (Specific Optical Rotation) : −56.3° (C=1 Methanol)
Proton NMR (300 MHz, CDCl3) δ PPM 7.77-7.82 (m, 2H), 7.38-7.53 (m, 3H), 7.02-7.05 (d, 1H), 4.89-4.95 (m, 1H), 3.80 (s, 3H), 3.60-3.65 (t, 2H), 2.43-2.53 (m, 1H), 2.25-2.35 (m, 1H)
Carbon NMR (CDCl3) δ PPM 172.49, 167.55, 133.68, 132.22, 128.87, 127.36, 53.05, 51.02, 40.93, 35.28

Example 2: Synthesis of (S)-2-Benzoylamino 4-chloro 1-Butanol (4)

(S)-2-Benzoylamino 4-chloro Butyric acid methyl ester (3) (23g, 0.09 mol) is taken in ethanol (200 ml) and stirred to get a clear solution. The solution is cooled to 10-15° C. and sodium borohydride (3.4 g, 0.09 mol) is added portion wise over a period of 45 minutes controlling the temperature by external cooling.

After complete addition, the reaction mixture is allowed to stir at its own temperature for 5 hours. The completion of the reaction is checked by TLC analysis whereby the absence of the starting material is confirmed. Once the reaction is over, the reaction mixture is cooled and quenched by the addition of water. Then the pH is adjusted to 2-3 using dil. HCl. The product is extracted by MDC twice. The organic layer is washed with water twice followed by brine solution. Further it is dried over sodium sulfate and concentrated completely.

The crude product is purified by silica gel column chromatography using the mixture of Hexane and Ethyl acetate as eluent.
Yield: 12.5 g
Melting point: 116-118° C.
SOR: −67.1° (C=1, Methanol)
Proton NMR (300 MHz, CD3OD) δ PPM 8.2-8.25 (d, 1H), 7.80-7.85 (d, 2H), 7.40-7.55 (in, 3H), 4.25-4.40 (m, 1H), 3.60-3.70 (m, 4H), 2.00-2.23 (m, 2H)
Carbon NMR (CD3OD) δ PPM 169.39, 134.62, 131.51, 128.35, 127.24, 63.59, 49.99, 41.51, 34.17

Example 3: Synthesis of (S)-3-Benzoylamino Tetrahydrofuran (5)

(S)-2-Benzoylamino 4-chloro 1-Butanol (4) (12.5g, 0.055 mol) is taken in Methanol and cooled to 15-20° C. Sodium hydroxide (3.5g) is added in lots over a period of 30 minutes and the reaction mixture is stirred at room temperature for 10 hours. The completion of the reaction is confirmed by TLC analysis.

Once the reaction is complete, the mixture is concentrated under vacuum to remove methanol and diluted with water followed by acidification to pH 2-3 using dil. HCl. The product is extracted with methylene dichloride. The organic layer is washed with water twice followed by brine solution. The organic layer is dried over sodium sulfate and concentrated completely. The solid product is stirred with hexane and filtered. The product is dried under vacuum.
Yield: 10 g
Melting point: 106 -108° C.
SOR: −29.4° (c=1, methanol)
Proton NMR (300 MHz, CDCl3) δ PPM7.77-7.80 (d, 2H), 7.30-7.55 (m, 3H), 6.65-6.70 (d,1H), 4.60-4.70 (m, 1H), 3.75-3.98 (m, 4H), 2.26-2.36 (m, 1H), 1.90-1.97 (m, 1H)
Carbon NMR (75 MHz, CDCl3) δ PPM167.61, 134.46, 131.79, 128.75, 127.19, 73.68, 67.19, 51.03, 33.40

Example 4: Synthesis of (S)-3-Amino Tetrahydrofuran Hydrochloride (6)

(S)-3-Benzoylamino-tetrahydrofuran (5) (20.0 g, 0.105 mol) was dissolved in ethanol (~40 ml) after which sodium hydroxide solution (25 g sodium hydroxide in 120 ml water) was added. The reaction mixture was heated at reflux for 9-10 h, after which TLC showed the absence of starting material. The reaction mixture was cooled to room temperature and was then acidified with dilute HCl. The precipitated benzoic acid was filtered off and the aqueous layer washed with methylene dichloride and concentrated completely to give a material which is mixed with the salt. Isopropanol was added and stirred for 1 h at room temperature. The salt was filtered off and the reaction mass was concentrated completely to give a pasty material. This was then stirred with isopropyl alcohol to crystallize out the material, which was then filtered, washed with chilled isopropyl alcohol, and dried under vacuum.
Yield: 11 g
Melting point: 165-170° C.
SOR: −10.2 (c=1, methanol)
Proton NMR (300 MHz, D2O) δ PPM3.80-4.11 (m, 5H), 2.37-2.5 (m, 1H), 2.01-2.09 (m, 1H)
Carbon NMR (D2O) δ PPM70.49, 66.82, 51.21, 30.01

Example 5: Synthesis of (S)-2-Benzyloxycarbonylamino 4-chloro Butyric Acid Methyl Ester (8)

Dry methanol (250 ml) is taken and cooled to 0-5° C. Acetyl chloride (39.25 g, 0.5 mol) is added drop wise at that temperature and stirred for 15 minutes. (S)-2-Benzyloxycarbonylamino γ-Butyrolactone (7) (23.52 g, 0.1 mol) is added portion wise at >10° C. over a period of 30 minutes. The clear solution is stirred at RT for 15 hours for the complete reaction. The completion is confirmed by TLC analysis.

Once the reaction is complete, methanol is removed by distillation under vacuum and ice water is added. The product is extracted using MDC and the organic layer is washed with water twice followed by brine solution. The organic layer is dried over sodium sulfate and concentrated completely. The product is precipitated by stirring with Hexane and filtered. Dried under vacuum to get the white solid product.
Yield: 27 g
Melting point: 46-48° C.
SOR: −50.7° (C=1, Methanol)
Proton NMR (300 MHz, CDCl3) δ PPM 7.30-7.40 (m, 5H), 5.45-5.55 (d, 1H), 5.11 (s, 2H), 4.45-4.60 (m, 1H), 3,75 (s, 3H), 3.55-3.60 (t, 2H), 2.05-2.40 (m, 2H)
Carbon NMR (CDCl3) δ PPM 172.36, 156.16, 136.27, 128.80, 128.52, 128.39, 67.43, 52.94, 52.02, 40.68, 35.49

Example 6: Synthesis of (S)-2-Benzyloxycarbonylamino 4-chloro 1-Butanol (9)

(S)-2-Benzyloxycarbonylamino 4-chloro butyric acid methyl ester (8) (25g, 0.0875 mol) is taken in Ethanol (200 ml) and stirred to get a clear solution. The solution is cooled to 10-15° C. and sodium borohydride (3.35 g, 0.0875 mol)

is added portion wise over a period of 45 minutes controlling the temperature by external cooling.

After complete addition, the reaction mixture is allowed to stir at its own temperature for 5 hours. The completion of the reaction is checked by TLC analysis whereby the absence of the starting material is confirmed. Once the reaction is over, the reaction mixture is cooled and quenched by the addition of water. Then the pH is adjusted to 2-3 using dil. HCl. The product is extracted by methylene dichloride twice. The organic layer is washed with water twice followed by brine solution. Further it is dried over sodium sulfate and concentrated completely.

The crude product is purified by silica gel column chromatography using the mixture of Hexane and Ethyl acetate as eluent.

Yield: 13.5 g
Melting point: 65-68° C.
SOR: −38.9° (C=1, Methanol)
Proton NMR (300 MHz, CDCl3) δ PPM 7.30-7.40 (m, 5H), 5.15-5.25 (d, 1H), 5.10 (s, 2H), 3.85-3.95 (m, 1H), 3.50-3.75 (m, 4H), 1.90-2.05 (m, 2H)
Carbon NMR (CDCl3) δ PPM 156.60, 136.16, 128.57, 128.26, 128.12, 67.02, 64.67, 50.85, 41.56, 34.28

Example 7: Synthesis of (S)-3-Benzyloxycarbonylamino Tetrahydrofuran (10)

(S)-2-Benzyloxycarbonylamino 4-chloro 1-butanol (9) (13.5 g, 0.052 mol) is taken in methanol and cooled to 15-20° C. Sodium hydroxide (3.5 g) is added in lots over a period of 30 minutes and the reaction mixture is stirred at room temperature for 10 hours. The completion of the reaction is confirmed by TLC analysis.

Once the reaction is complete, the mixture is concentrated under vacuum to remove methanol and diluted with water followed by acidification to pH 2-3 using dil. HCl. The product is extracted with methylene dichloride. The organic layer is washed with water twice followed by brine solution. The organic layer is dried over sodium sulfate and concentrated completely. The solid product is stirred with hexane and filtered. The product is dried under vacuum.

Yield: 11 g
Melting point: 53-55° C.
SOR: −12.4° (c=1 Methanol)
Proton NMR (300 MHz, CDCl3) δ PPM 7.28-7.38 (m, 5H), 5.30-5.40 (d, 1H), 5.07-5.09 (s, 2H), 4.20-4.40 (m, 1H), 3.50-3.90 (m, 4H), 2.03-2.23 (m,1H), 1.70-1.90 (m, 1H)
Carbon NMR (CDCl3) δ PPM 156.17, 136.63, 128.77, 128.41, 128.37, 73.62, 67.00, 52.03, 33.36

Example 8: Synthesis of (S)-3-Amino Tetrahydrofuran Hydrochloride (6) from (10)

(S)-3-Benzyloxycarbonylamino tetrahydrofuran (10) (39) (22.1g, 0.1 mol) is taken in methanol (200 ml) with palladium/carbon 5% (1.1g). The mixture is charged in an autoclave and hydrogenated at ambient temperature with a hydrogen pressure of 3 kg. The pressure is maintained with hydrogen at ambient temperature for 5 hours. TLC showed the completion of the reaction.

The mixture is filtered to remove the insoluble material. Dilute hydrochloric acid (15 ml) is added to the filtrate and concentrated completely under vacuum at <50° C. To the crude product, isopropyl alcohol (50 ml) is added and stirred to precipitate the product, (S)-3-amino tetrahydrofiiran hydrochloride (6) (16) as crystalline powder. The mixture is cooled for 5 hours at 0-5° C. and filtered. The product is washed with chilled isopropyl alcohol and dried under vacuum.

Yield: 9.25 g
The other analysis data matched with that detailed in Example 4.

Example 9: Synthesis of (S)-3-Benzoylamino tetrahydrofuran (5) from (3)

(Single step without isolation of (4))

(S)-2-Benzoylamino 4-chloro butyric acid methyl ester (3) (23 g, 0.09 mol) is taken in ethanol (200 ml) and stirred to get a clear solution. The solution is cooled to 10-15° C. and sodium borohydride (3.4 g, 0.09 mol) is added portion wise over a period of 45 minutes controlling the temperature by external cooling.

After complete addition, the reaction mixture is allowed to stir at its own temperature for 5 hours. The completion of the reaction is checked by TLC analysis whereby the absence of the starting material is confirmed.

Now sodium hydroxide (4.0 g, 0.1 mol) is added in lots to the reaction mixture over a period of 30 minutes. Further the reaction mixture is stirred at 45-50° C. for 5 hours for complete cyclization.

Once the reaction is over, the reaction mixture concentrated under vacuum and quenched by the addition of ice cold water. Then the pH is adjusted to 2-3 using dil. HCl. The product is extracted by methylene dichloride twice. The organic layer is washed with water twice followed by brine solution. Further it is dried over sodium sulfate and concentrated completely. Hexane is added to precipitate the product and filtered.

Yield: 15 g
The other analysis data matched with the same product obtained in Example 3

Example 10: Synthesis of (S)-3-Benzyloxycarbonylamino Tetrahydrofuran (10) from (8)

(Single step without isolation of intermediate (9))

(S)-2-Benzyloxycarbonylamino 4-chloro butyric acid methyl ester (8) (25g, 0.0875 mol) is taken in ethanol (200 ml) and stirred to get a clear solution. The solution is cooled to 10-15° C. and sodium borohydride (3.35g, 0.0875 mol) is added portion wise over a period of 45 minutes controlling the temperature by external cooling.

After complete addition, the reaction mixture is allowed to stir at its own temperature for 5 hours. The completion of the reaction is checked by TLC analysis whereby the absence of the starting material is confirmed.

Now sodium hydroxide (4.0 g, 0.1 mol) is added in lots to the reaction mixture over a period of 30 minutes. Further the reaction mixture is stirred at 45-50° C. for 5 hours for complete cyclization.

Once the reaction is over, the reaction mixture concentrated under vacuum and quenched by the addition of ice cold water. Then the pH is adjusted to 2-3 using dil. HCl. The product is extracted by methylene dichloride twice. The organic layer is washed with water twice followed by brine solution. Further it is dried over sodium sulfate and concentrated completely. Hexane is added to precipitate the product and filtered.

Yield: 17.5 g
The other analysis data matched with the same product obtained in Example 7

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A process for the preparation of (S)-3-Aminotetrahydrofuran hydrochloride represented by formula (I),

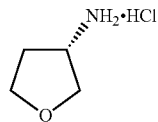
(I)

consisting steps of
a) reacting (S)-2-aroylamino gamma-butyrolactone represented by the formula (II) with an acid halide/alcohol to get alkyl-(S)-2-aroylamino 4-halo butanoate represented by the formula (III);

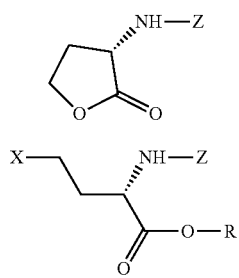

wherein,
Z is selected from group consisting of benzoyl, o-, m-, p-methylbenzoyl, o-, m-, p-chlorobenzoyl, o-, m-, p-methoxybenzoyl and p-toluenesulphonyl;
R is selected from group consisting of methyl, ethyl, n-propyl, isopropyl, butyl and isobutyl;
b) reducing alkyl-(S)-2-aroylamino 4-halo butanoate of formula (III) using metal borohydride in a solvent to provide (S)-2-aroylamino 4-halo-1-butanol represented by the formula (IV):

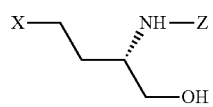
(IV)

wherein,
X is selected from group consisting of Cl and Br;
c) cyclizing (S)-2-Aroylamino 4-halo-1-butanol of formula (IV) using a base to obtain (3)-aroylamino tetrahydrofuran represented by the formula (V):

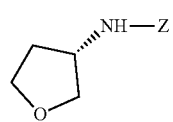
(V)

wherein,
d) removing the aroyl group of (3)-Aroylamino tetrahydrofuran with the formula (V) using metal hydroxide/alcohol medium followed by treatment with aqueous hydrochloric acid to get (S)-3-aminotetrahydrofuran hydrochloride represented by the formula (I):

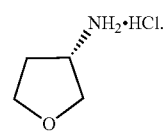
(I)

2. A process according to claim 1, wherein acid halide in step (a) is selected from group consisting of acetyl chloride, acetyl bromide, thionyl chloride, thionyl bromide, propionyl chloride, propionyl bromide, butyryl chloride, butyryl bromide, isobutyryl chloride and isobutyryl bromide.

3. A process according to claim 1, wherein alcohol in step (a) is selected from group consisting of methanol, ethanol, n-propanol, isopropanol, butanol, isobutanol and sec.butanol.

4. A process according to claim 1, wherein metal borohydride in step (b) is selected from group consisting of lithium borohydride, sodium borohydride, potassium borohydride and zinc borohydride.

5. A process according to claim 1, wherein solvent in step (b) is selected from group consisting of methanol, ethanol, n-propanol and isopropanol.

6. A process according to claim 1, wherein the base in step (c) is selected from group consisting of sodium hydroxide, potassium hydroxide, sodium carbonate, potassium carbonate, calcium hydroxide, barium hydroxide, magnesium hydroxide, triethylamine, diisopropyl ethylamine, pyridine and 4-dimethylamino pyridine.

7. A process according to claim 1, wherein the metal hydroxide in step (d) is selected from group consisting of sodium hydroxide, potassium hydroxide, calcium hydroxide, barium hydroxide and magnesium hydroxide.

8. A process for the preparation of compound with formula (V)

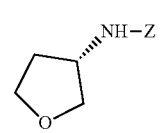
(V)

consisting step of reducing alkyl-(S)-2-aroylamino 4-halo butanoate of formula (III) using a metal borohydride in a solvent and cyclising using a base to obtain (3)-aroylamino tetrahydrofuran as represented by the formula (V)

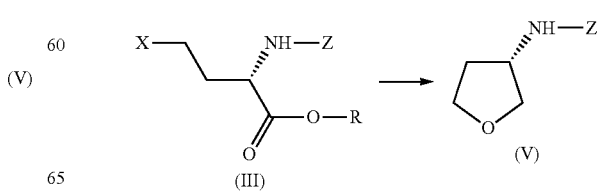

wherein,
Z is selected from group consisting of benzoyl, o-, m-, p-methylbenzoyl, o-, m-, p-chlorobenzoyl,o-, m-, p-methoxybenzoyl and p-toluenesulphonyl; the metal borohydride is selected from group consisting of lithium borohydride, sodium borohydride, potassium borohydride and zinc borohydride; the solvent is selected from group consisting of methanol, ethanol, n-propanol and isopropanol, and the base is selected from group consisting of sodium hydroxide, potassium hydroxide, sodium carbonate, potassium carbonate, calcium hydroxide, barium hydroxide, magnesium hydroxide, triethylamine, diisopropyl ethylamine, pyridine and 4-dimethylamino pyridine.

9. A compound represented by the formula (VI)

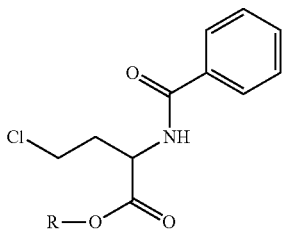
(VI)

wherein,
R in formula (VI) is selected from group consisting of —CH3 and —C2H5.

10. The compound of the formula (VIII), 2-Benzoylamino 4-halo 1-butanol

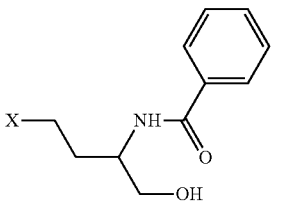
(VIII)

wherein,
X in formula (VIII) is selected from group consisting of Cl and Br.

11. A process for the preparation of (S)-3-Aminotetrahydrofuran hydrochloride represented by formula (I),

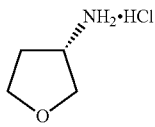
(I)

consisting steps of
a) reacting (S)-2-benzyloxycarbonylamino gamma-butyrolactone represented by the formula (X) with an acid halide/alcohol to get alkyl (S)-2-benzyloxycarbonylamino-4-halo butanoate represented by the formula (XI);

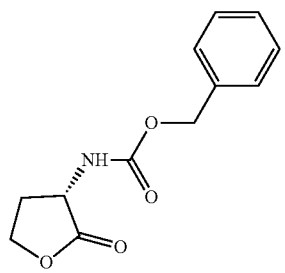
(X)

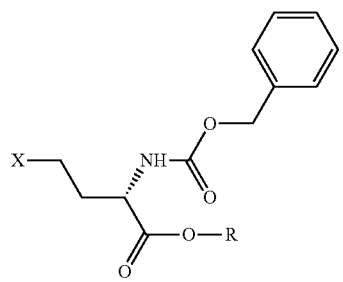
(XI)

wherein,
R is selected from group consisting of methyl, ethyl, n-propyl, isopropyl, butyl and isobutyl;
X is selected from group consisting of from Cl and Br;
b) reducing alkyl (S)-2-benzyloxycarbonylamino 4-halo butanoate of formula (XI) using metal borohydride in a solvent to provide (S)-2-benzyloxycarbonyl- 4-halo 1-butanol represented by the formula (XII):

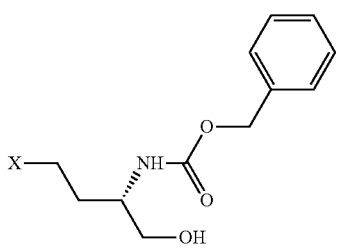
(XII)

c) cyclizing (S)-2-benzyloxycarbonyl 4-halo- 1-butanol of formula (XII) using a base to obtain (S)-benzyoxycarbonylamino tetrahydrofuran represented by the formula (XIII):

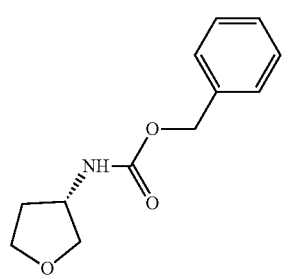
(XIII)

d) removing the benzyloxycarbonyl group of (S)-benzyoxycarbonylamino tetrahydrofuran represented by the formula (XIII) using Palladium/carbon or Raney nickel under hydrogen atmosphere in alcohol medium followed by separation of the catalyst and subsequent treatment with aqueous hydrochloric acid to get (S)-3-Aminotetrahydrofuran hydrochloride represented by the formula (I),

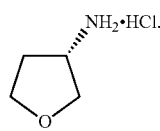

(I)

12. A process according to claim 11, wherein acid halide in step (a) is selected from group consisting of acetyl chloride, acetyl bromide, thionyl chloride, thionyl bromide, propionyl chloride, propionyl bromide, butyryl chloride, butyryl bromide, isobutyryl chloride and isobutyryl bromide.

13. A process according to claim 11, wherein alcohol in step (a) is selected from group consisting of methanol, ethanol, n-propanol, isopropanol, butanol, isobutanol and sec.butanol.

14. A process according to claim 11, wherein metal borohydride in step (b) is selected from group consisting of lithium borohydride, sodium borohydride, potassium borohydride and zinc borohydride.

15. A process according to claim 11, wherein solvent in step (b) is selected from group consisting of methanol, ethanol, n-propanol and isopropanol.

16. A process according to claim 11, wherein the base in step (c) is selected from group consisting of sodium hydroxide, potassium hydroxide, sodium carbonate, potassium carbonate, calcium hydroxide, barium hydroxide, magnesium hydroxide, triethylamine, diisopropyl ethylamine, pyridine and 4-dimethylamino pyridine.

17. The compound of the formula (IX), 2-Benzyloxycarbonylamino-4-halo 1-butanol

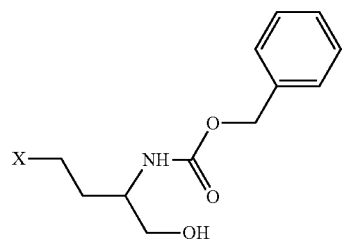

(IX)

wherein,
X in formula (IX) is selected from group consisting of Cl and Br.

18. A process for the preparation of the compound of formula (XIII)

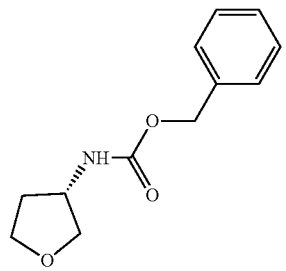

(XIII)

consisting step of reducing compound of formula (X1) using a metal borohydride in a solvent and cyclising using a base to obtain the compound of formula (XIII),

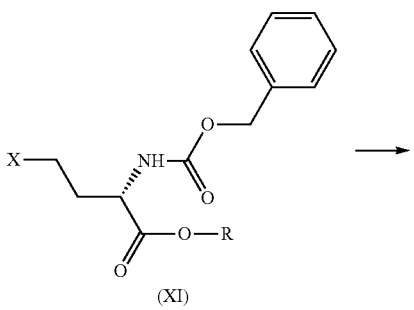

(XI)

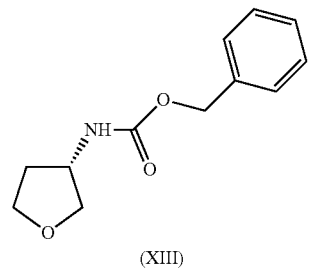

(XIII)

wherein,
the metal borohydride is selected from group consisting of lithium borohydride, sodium borohydride, potassium borohydride and zinc borohydride; the solvent is selected from group consisting of methanol, ethanol, n-propanol and isopropanol, and the base is selected from group consisting of sodium hydroxide, potassium hydroxide, sodium carbonate, potassium carbonate, calcium hydroxide, barium hydroxide, magnesium hydroxide, triethylamine, diisopropyl ethylamine, pyridine and 4-dimethylamino pyridine.

* * * * *